(12) United States Patent
Baudry et al.

(10) Patent No.: US 8,798,341 B2
(45) Date of Patent: Aug. 5, 2014

(54) METHOD AND DEVICE FOR READING AN EMULSION

(75) Inventors: Jean Baudry, Paris (FR); Julien Sylvestre, Paris (FR); Jerome Bibette, Paris (FR); Laurent Boitard, Paris (FR); Nicolas Bremond, Paris (FR)

(73) Assignees: Universite Pierre et Marie Curie (Paris 6), Paris (FR); Centre National de la Recherche Scientifique, Paris (FR); Universite Paris Diderot-Paris 7, Paris (FR)

( * ) Notice: Subject to any disclaimer, the term of this patent is extended or adjusted under 35 U.S.C. 154(b) by 798 days.

(21) Appl. No.: 13/054,194

(22) PCT Filed: Jul. 13, 2009

(86) PCT No.: PCT/FR2009/051396
§ 371 (c)(1),
(2), (4) Date: Mar. 23, 2011

(87) PCT Pub. No.: WO2010/007307
PCT Pub. Date: Jan. 21, 2010

(65) Prior Publication Data
US 2011/0188717 A1    Aug. 4, 2011

(30) Foreign Application Priority Data
Jul. 15, 2008   (FR) ...................................... 08 04024

(51) Int. Cl.
*G06K 9/00* (2006.01)

(52) U.S. Cl.
USPC ........... 382/128; 382/278; 382/282; 382/307; 128/922; 128/923

(58) Field of Classification Search
USPC ........... 382/128, 278, 282, 307; 128/922, 923
See application file for complete search history.

(56) References Cited

U.S. PATENT DOCUMENTS

| 7,307,104 B2 | 12/2007 | Qiu et al. |
| 7,578,916 B2 * | 8/2009 | Bryning ........................ 204/451 |

(Continued)

FOREIGN PATENT DOCUMENTS

WO    2008/121342 A    10/2008

OTHER PUBLICATIONS

Keng-Shiang Huang et al: "Calcium alginate microcapsule generation on a microfluidic system fabricated using the optical disk process; Calcium alginate microcapsule generation on a microfluidic system", Journal of Micromechanics &Microengineering,Institute of Physics Publishing, Aug. 1, 2007, pp. 1428-1434, Bristol, GB, XP020120175.

(Continued)

*Primary Examiner* — Yosef Kassa
(74) *Attorney, Agent, or Firm* — Young & Thompson (57) ABSTRACT

A method for reading an emulsion (3) including droplets and a continuous phase surrounding the droplets, the method includes:
two-dimensional scanning of the emulsion (3), and
construction of a two-dimensional image of the emulsion (3) based on the scanning. Preferably, the droplets do not move during scanning, for example by solidifying the continuous phase or by using a two-dimensional compact or semi-compact network of droplets. The method can further include time-based monitoring of a chemical or biological reaction taking place in at least one of the droplets. A device implementing this method is also described. The method is applicable for the detection and/or sorting of microdroplets performing the role of microreactors or containing specific cells or molecules, in fields such as gene expression or diagnosis.

72 Claims, 6 Drawing Sheets

(56) References Cited

U.S. PATENT DOCUMENTS

| | | | |
|---|---|---|---|
| 7,897,342 B2 * | 3/2011 | Bing et al. | 435/6.13 |
| 7,906,286 B2 * | 3/2011 | Fukui et al. | 435/6.15 |
| 7,968,287 B2 * | 6/2011 | Griffiths et al. | 435/6.1 |
| 8,049,001 B2 * | 11/2011 | Tomatsu et al. | 536/24.32 |
| 8,263,043 B2 * | 9/2012 | Ahrens et al. | 424/9.34 |
| 8,283,308 B2 * | 10/2012 | Mason et al. | 514/1.1 |
| 8,315,821 B2 * | 11/2012 | Brujic et al. | 702/30 |
| 8,334,013 B2 * | 12/2012 | Petsev et al. | 427/212 |
| 8,409,807 B2 * | 4/2013 | Neely et al. | 435/6.12 |
| 8,535,889 B2 * | 9/2013 | Larson et al. | 435/6.12 |
| 2002/0058332 A1 | 5/2002 | Quake et al. | |
| 2002/0198928 A1 | 12/2002 | Bukshpan et al. | |
| 2005/0221339 A1 | 10/2005 | Griffiths et al. | |
| 2006/0078888 A1 | 4/2006 | Griffiths et al. | |
| 2007/0054119 A1 | 3/2007 | Garstecki et al. | |
| 2008/0124726 A1 | 5/2008 | Monforte | |

OTHER PUBLICATIONS

Kobayashi I et al: "Formulation of monodisperse emulsions using submicron-channel arrays", Colloids and Surfaces. A, Physicachemical and Engineering Aspects, Mar. 15, 2007, pp. 285-289, vol. 296, No. 1-3, Elsevier, Amsterdam, NL,XP022670909.

International Search Report, Dated Feb. 22, 2010, in PCT/FR2009/051396.

* cited by examiner

METHOD AND DEVICE FOR READING AN EMULSION

FIELD OF INDUSTRY

The present invention relates to a method for reading an emulsion. It also relates to a device for reading an emulsion employing the method according to the invention. In this document, "reading an emulsion" generally means extraction of information from this emulsion.

Non-limitative examples of application of the invention are the detection and/or sorting of microdroplets, which can perform the role of chemical or biological microreactors or can contain cells or specific molecules, in areas such as gene expression or diagnosis.

PRIOR ART

The water droplets in a water-in-oil inverted emulsion constitute micro-compartments that can perform the role of independent chemical or biochemical microreactors and can make it possible to carry out numerous reactions in parallel.

A first type of reaction relates to the expression of a single gene per droplet and the field of directed evolution. Starting from a library of genes coding for example for variants of an enzyme, these genes are expressed and the droplets are sorted on the basis of the activity of these enzyme variants (for example, by fluorescence). Two techniques have been described that permit high-throughput sorting of these libraries of droplets: microfluidics and flow cytometry. These techniques are complex, requiring a specialized experimenter and specialized equipment. Microfluidics is still at the development stage and a Fluorescence Activated Cell Sorter (FACS) costs several hundred thousand euros. During experiments using a FACS, water-in-oil-in-water double emulsions are used in order to have an aqueous continuous phase and this makes the formulation more complicated. The maximum throughputs obtained with these techniques of FACS or of microfluidics that sort droplets one by one are from 1000 to 10000 droplets per second. Therefore the throughputs achieved with these existing techniques are insufficient for sorting genome libraries.

A second field of application of emulsions considered as microreactors is diagnosis and more generally the detection of molecules. Once again, the throughput is fundamental, as this is what will determine the sensitivity of the test.

The purpose of the present invention is to propose a method and a device for reading an emulsion more rapidly than in the state of the art.

DESCRIPTION OF THE INVENTION

This objective is achieved with a method for reading an emulsion comprising droplets, said method comprising:
  two-dimensional scanning of the emulsion by an optical system,
  construction of a two-dimensional image of the emulsion based on said scanning.

The emulsion comprises a continuous phase surrounding the droplets. The continuous phase preferably comprises oil, and the droplets preferably comprise water.

The emulsion can be an inverted emulsion of water droplets in an oil continuous phase, a direct emulsion of oil droplets in a water continuous phase, a double emulsion of water droplets in oil droplets in a water continuous phase, or a double emulsion of oil droplets in water droplets in an oil continuous phase.

Preferably, the droplets do not move during scanning, i.e. the droplets are "frozen" during scanning.

Preferably, the droplets are said to be frozen or do not move during a scan if during this scanning each droplet moves in the emulsion by a distance less than its diameter:
  in the case of the solidified continuous phase described hereinafter, this displacement is zero, and
  in the case of a two-dimensional network of droplets described hereinafter, this displacement depends on the volume fraction of the droplets in the emulsion and is almost zero (colloidal solid) when this volume fraction exceeds a threshold, typically equal to 60%.

In particular, when scanning of the emulsion is repeated periodically several times, for example for periodic construction of the two-dimensional image of the droplet or for time-based monitoring, the droplets are said to be frozen if during a period of repetition of scanning each droplet moves in the emulsion by a distance less than its diameter.

The continuous phase is preferably solid during scanning, preferably at ambient temperature. Thus, the droplets of the emulsion can be frozen during scanning by solidifying the continuous phase surrounding them. In this variant, the continuous phase is solidified in order to freeze the droplets within the solidified continuous phase.

The continuous phase can have a melting point above 37° C., preferably above 40° C., more preferably above 50° C.

During scanning of the emulsion, the emulsion is preferably kept at a temperature below the melting point of the continuous phase. Thus, in this variant, the continuous phase can be solid during scanning depending on its temperature.

In other variants, to solidify the continuous phase, this continuous phase can be solidified by cross-linking, for example:
  by using a continuous phase that cross-links when it is irradiated for example with ultraviolet radiation, and by subjecting this continuous phase to said radiation before scanning, for example the UV epoxy resin called NOA60 from Norland Optical, or a mixture comprising 96 wt. % of ethylene glycol dimethacrylate (EGDMA) and 4 wt. % of 1-hydroxycyclohexyl phenyl ketone (HCPK) photoinitiator, or
  by using a continuous phase that comprises a mixture of two components that cross-link before scanning, for example an epoxy resin that cross-links at ambient temperature or on being heated.

The droplets of the emulsion can form a two-dimensional network of droplets. In this variant, the emulsion can comprise a high droplet density or fraction so that the droplets are blocked by one another, and the droplets can thus be frozen, forming a compact or semi-compact network of droplets. The volume fraction of droplets in the emulsion can be greater than or equal to 40%, preferably greater than or equal to 60%. The droplets of the emulsion can form a colloidal solid.

The continuous phase preferably comprises a surfactant.

During scanning of the emulsion, the emulsion can be stored in a receptacle, and:
  during scanning of the emulsion, the receptacle can be maintained at a roughly constant temperature, preferably to an accuracy of plus or minus 0.1° C., and/or
  the receptacle can comprise a flat wall which is in contact with the emulsion during scanning of the emulsion and is arranged horizontally with a vertical difference in level of less than 5 micrometers over a horizontal distance of 2 centimeters, and/or
  the receptacle can comprise two approximately parallel surfaces, which hold each of the droplets in place during scanning of the emulsion.

The method according to the invention can further comprise time-based monitoring of a chemical or biological reaction taking place in at least one of the droplets, said monitoring comprising repetition of the steps of scanning and construction.

Moreover, the method according to the invention can further comprise locating droplets comprising a given type of molecule or cell by analysing the two-dimensional image of the emulsion. Locating can comprise the use of an algorithm for thresholding and segmentation of the two-dimensional image.

The method according to the invention can further comprise sampling of droplets comprising the given type of molecule or cell. Sampling can comprise for example:
 movement of an end of a micropipette to coordinates where a droplet comprising the given type of molecule or cell has been located, and
 aspiration of this droplet by the micropipette.

The method according to the invention can further comprise counting of droplets comprising a given type of molecule or cell by analysing the two-dimensional image of the emulsion. Counting can comprise the use of an algorithm for thresholding and segmentation of the two-dimensional image.

The construction of the two-dimensional image preferably comprises, during scanning:
 projection of different partial images of the emulsion via the optical system onto a detector,
 combining the different partial images of the emulsion acquired by the detector.

The partial images are preferably images of fluorescence signals emitted by the emulsion.

The emulsion is preferably an inverted emulsion of water droplets in oil.

The emulsion is preferably spread out to give a thickness between 1 and 100 layers of droplets.

The optical system can have a depth of field roughly equal to or greater than the thickness of the spread-out emulsion.

The method according to the invention can further comprise:
 placement of the emulsion between two parallel plates, at least one of which is transparent to permit construction of the two-dimensional image,
 a shearing movement between the two plates until the emulsion is monodisperse.

In this document, an emulsion is said to be monodisperse when the standard deviation of the distribution of the diameters of the droplets within this emulsion is less than 30% of the mean value of the diameters of these droplets.

According to yet another aspect of the invention, a device for reading an emulsion comprising droplets is proposed, said device employing the method according to the invention and comprising:
 a receptacle for receiving the emulsion,
 an optical system,
 means for carrying out two-dimensional scanning of the emulsion by the optical system,
 means for constructing a two-dimensional image of the emulsion based on a two-dimensional scan of the emulsion.

The emulsion comprises a continuous phase surrounding the droplets.

The device according to the invention can comprise means for "freezing" the droplets during scanning, i.e. means for ensuring that the droplets do not move during scanning.

The device according to the invention can comprise means for solidifying the continuous phase during scanning.

The continuous phase can have a given melting point, and the device according to the invention can comprise means for keeping the emulsion at a temperature below the melting point of the continuous phase during scanning of the emulsion. Thus, in this variant, the solidifying means can comprise means for maintaining the temperature.

In other variants, the solidifying means can comprise means for solidifying the continuous phase by cross-linking, for example, if the continuous phase is formulated for cross-linking when it is subjected to radiation, for example to ultra-violet radiation, means for subjecting this continuous phase to such radiation for cross-linking the continuous phase or more generally means for subjecting the emulsion to such cross-linking radiation, or if the continuous phase is formulated for cross-linking on being heated, means for heating this continuous phase or more generally means for heating the emulsion.

The device according to the invention can comprise means for the production of the emulsion arranged so that the droplets of the emulsion form a two-dimensional network of droplets, preferably having a volume fraction of droplets in the emulsion greater than or equal to 40%, more preferably greater than or equal to 60%, and preferably forming a colloidal solid. The means for production preferably comprise a chamber for creaming or sedimentation of the droplets and means for sampling, from said chamber, droplets diluted in the continuous phase according to a given volume fraction of droplets.

Moreover, the device according to the invention can comprise means for maintaining the receptacle at a roughly constant temperature during scanning of the emulsion, preferably to an accuracy of plus or minus 0.1° C.

The receptacle can comprise a flat wall arranged so that it is in contact with the emulsion during scanning of the emulsion and arranged horizontally with a vertical difference in level of less than 5 micrometers over a horizontal distance of 2 centimeters.

The receptacle can comprise two approximately parallel surfaces arranged to hold each of the droplets in place during scanning of the emulsion.

The device according to the invention can further comprise means for time-based monitoring of a chemical or biological reaction taking place in at least one of the droplets.

Moreover, the device according to the invention can further comprise means for locating droplets comprising a given type of molecule or cell, the locating means comprising means for analysis of the two-dimensional image of the emulsion.

The device according to the invention can further comprise means for sampling droplets comprising the given type of molecule or cell. The sampling means can for example comprise:
 a micropipette,
 means for moving an end of the micropipette to coordinates of a droplet comprising the given type of molecule or cell and located by the locating means, and
 means for aspirating this droplet by the micropipette.

Moreover, the device according to the invention can further comprise means for counting droplets comprising a given type of molecule or cell, the counting means comprising means for analysis of the two-dimensional image of the emulsion.

The means for constructing the two-dimensional image preferably comprise:
 a detector, onto which the optical system is arranged to project different partial images of the emulsion during a scan,
 means for combining different partial images of the emulsion acquired by the detector during scanning.

The partial images are preferably images of fluorescence signals emitted by the emulsion.

The receptacle can be arranged so that the emulsion is spread out inside the receptacle, preferably so as to have a thickness between 1 and 100 layers of droplets.

The optical system can have a depth of field roughly equal to or greater than the thickness of the spread-out emulsion.

Moreover, the receptacle preferably comprises two parallel plates, at least one of which is transparent, and means for applying a shearing movement between the two plates until the emulsion is monodisperse.

DESCRIPTION OF THE DRAWINGS AND EMBODIMENTS

Other advantages and particular features of the invention will become apparent on reading the detailed description of applications and embodiments, which are in no way limitative, and the following appended drawings.

Figure 1:
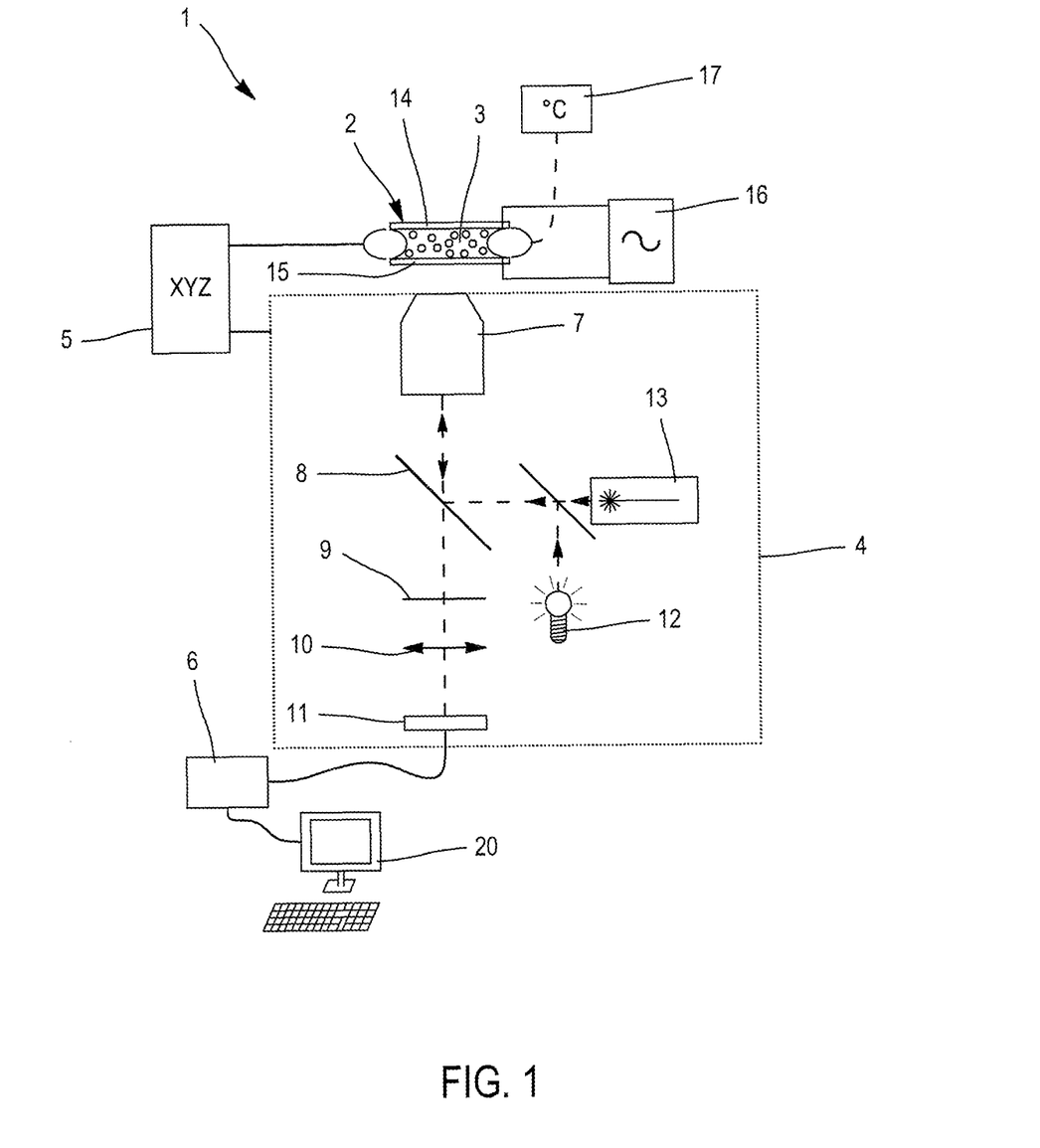
FIGS. 1 and 2 illustrate a preferred embodiment of the device according to the invention employing a method according to the invention.

A preferred embodiment of device 1 according to the invention employing a method according to the invention will be described, referring to FIGS. 1 to 3.

Device 1 comprises:
- a receptacle 2 for receiving an emulsion 3 that comprises droplets 21 and a continuous phase 23,
- an optical system 4, more particularly an optical microscopy system,
- a stage 5 motorized in three orthogonal directions X, Y, Z, arranged for moving the receptacle 2 and therefore the emulsion 3 relative to the optical system in the three directions X, Y and Z; we shall refer indiscriminately to the position of receptacle 2 or to the position of the emulsion 3. The stage 5 is in particular arranged for carrying out two-dimensional scanning of the emulsion 3 by the optical system 4,
- an analysis unit 6, typically comprising a central processing unit of a computer, a digital electronic circuit, an analogic electronic circuit, a microprocessor and/or software,
- a screen 20 connected to unit 6.

The receptacle 2 is composed of a material comprising for example a polymer such as polydimethylsiloxane (PDMS) or else glass.

Each droplet of the emulsion is roughly spherical and constitutes a tank that is isolated from the other droplets and in which a chemical or biological reaction or event can take place.

The phase 23 surrounds the droplets 21, i.e. it envelops the droplets, it is separate from the droplets 21, and is in contact with the perimeters of each of these droplets 21.

Moreover, phase 23 is said to be "continuous" because for any pair of points located in this phase 23, it is always possible to draw a line connecting these two points, said line not intersecting any of the droplets 21 but passing exclusively either through the continuous phase 23 or possibly through at least one junction point or line at the level of which the outer perimeters of two droplets 21 are tangential or in contact.

By "two-dimensional scanning of the emulsion 3 by the optical system 4" is meant relative displacement of the optical system 4 in relation to the emulsion in at least two orthogonal spatial directions X and Y, the directions X, Y typically being contained in a plane parallel to the emulsion 3, to the plates 14, 15 and to a focal plane of the optical system 4 (corresponding to the object focal plane of the objective lens 7).

The optical system 4 comprises:
- a microscope objective lens 7,
- a dichroic mirror 8,
- a dichroic filter 9,
- a set of lenses 10,
- a detector 11, typically consisting of a CCD camera,
- a source of white light 12 set up for illuminating the receptacle 2 and the emulsion 3, and
- an excitation laser 13, arranged so that it emits radiation onto the receptacle 2 and the emulsion 3.

In a variant, a mercury arc lamp equipped with an excitation filter can be used in place of the laser 13.

During scanning of the emulsion 3 by the optical system, the relative position of the emulsion 3 relative to the optical system 4 changes. The emulsion emits light, which is captured by the objective lens. This light is for example emitted by diffusion of white light received from source 12, and/or by emission of fluorescence following excitation of the emulsion by the laser 13. The light captured by the objective lens 7, originating from the emulsion, corresponds to a portion of the emulsion, and passes through mirror 8 and filter 9, and is then focused on the CCD camera 11 by the set of lenses 10. For each relative position of the emulsion 3 relative to the optical system 4, the camera 11 thus acquires a given partial image of the emulsion 3, this partial image corresponding to the portion of the emulsion imaged by the optical system 4 for this relative position. Thus, the optical system is arranged for projecting different partial images of the emulsion onto camera 11 during a scan of the emulsion by the optical system 4. The partial images can comprise partial images of the emulsion by fluorescence, by luminescence and/or in white light, depending on the nature of the light illuminating the emulsion and depending on the nature of filter 9. In a preferred embodiment, the partial images are images of fluorescence signals emitted by the emulsion.

As will be explained below, describing the method according to the invention in detail, the analysis unit 6 is arranged for:
- constructing a two-dimensional image of the emulsion based on a two-dimensional scan of the emulsion by the optical system 4 by means of stage 5, this construction being carried out by combining different partial images of the emulsion acquired by camera 11 during scanning;
- analysing a two-dimensional image of the emulsion constructed by this unit 6, so as to:

locate, in this two-dimensional image, specific droplets 22 comprising a given type of molecule or cell and determine the coordinates of each of the droplets 21, 22 in this two-dimensional image, and/or count, in this two-dimensional image, specific droplets 22 comprising a given type of molecule or cell;

time-based monitoring of a chemical or biological reaction taking place in at least one of the droplets, by storing and comparing successive two-dimensional images constructed by this unit 6.

By "two-dimensional image of the emulsion" is meant a set of data representing the emulsion (for example intensity, one or more colours, fluorescence signals, etc.) as a function of two orthogonal spatial coordinates X and Y. Typically, these data can be stored:

in graphical form in an image file of type JPEG, BITMAP, or other that can be displayed directly on screen 20, or in raw form in a data file such as a text file, a file of a spreadsheet or other.

Filter 9 is arranged so as to allow a specific fluorescence signal emitted by the specific droplets 22 to pass through, but to block the wavelengths emitted by the laser 13, so that the camera is set up for detecting this specific fluorescence signal. Unit 6 is arranged for recording this specific fluorescence signal, as forming part of the data of the two-dimensional image.

The receptacle comprises two parallel plates 14, 15, between which emulsion 3 is placed. These two plates 14, 15 are roughly parallel to a focal plane of the optical system 4, more particularly these two plates 14, 15 are roughly parallel to the object focal plane of the objective lens 7. One of these plates 15 is arranged so that it is positioned between the emulsion 3 and the optical system 4 (or the objective lens 7), and is transparent. The optical system 4 is arranged for imaging the emulsion 3 through this transparent plate 15 to permit construction of the two-dimensional image. The other plate 14 is positioned on the side opposite to the optical system 4 relative to the emulsion 3.

Moreover, receptacle 2 is arranged so that the emulsion is spread out between the two plates 14, 15 so as to have a thickness between 1 and 100 layers of droplets. In a preferred embodiment, the optical system 4 has a depth of field equal to the thickness of several layers of droplets 21, or even roughly equal to or greater than the total thickness of the spread-out emulsion, so that by scanning the emulsion just once, a two-dimensional image of the entire thickness of the emulsion is created.

The device 1 further comprises motorized means 16 arranged for applying a shearing movement between the two plates 14, 15 until the emulsion 3 is monodisperse.

The device 1 further comprises means 17 for maintaining the emulsion 3 at a constant temperature below the melting point of the continuous phase 23 during scanning of the emulsion. These maintaining means typically comprise:

a probe arranged for measuring the temperature of plate 14 and/or 15 and/or the temperature of the emulsion 3 directly, means for heating and/or cooling plate 14 and/or 15 and/or emulsion 3 directly, so as to control the temperature of the emulsion to constant temperature.

Finally, device 1 further comprises means for sampling specific droplets 22. The sampling means (only shown in FIG. 2) comprise:

a micropipette 18, a stage 19 motorized in three orthogonal directions X, Y, Z, arranged for moving the micropipette relative to receptacle 2 and emulsion 3 in the three directions X, Y and Z, and for moving an end of the micropipette to coordinates of a specific droplet 22 located by unit 6, and suction means (not shown) arranged for aspirating this droplet along the micropipette.

Figure 2:
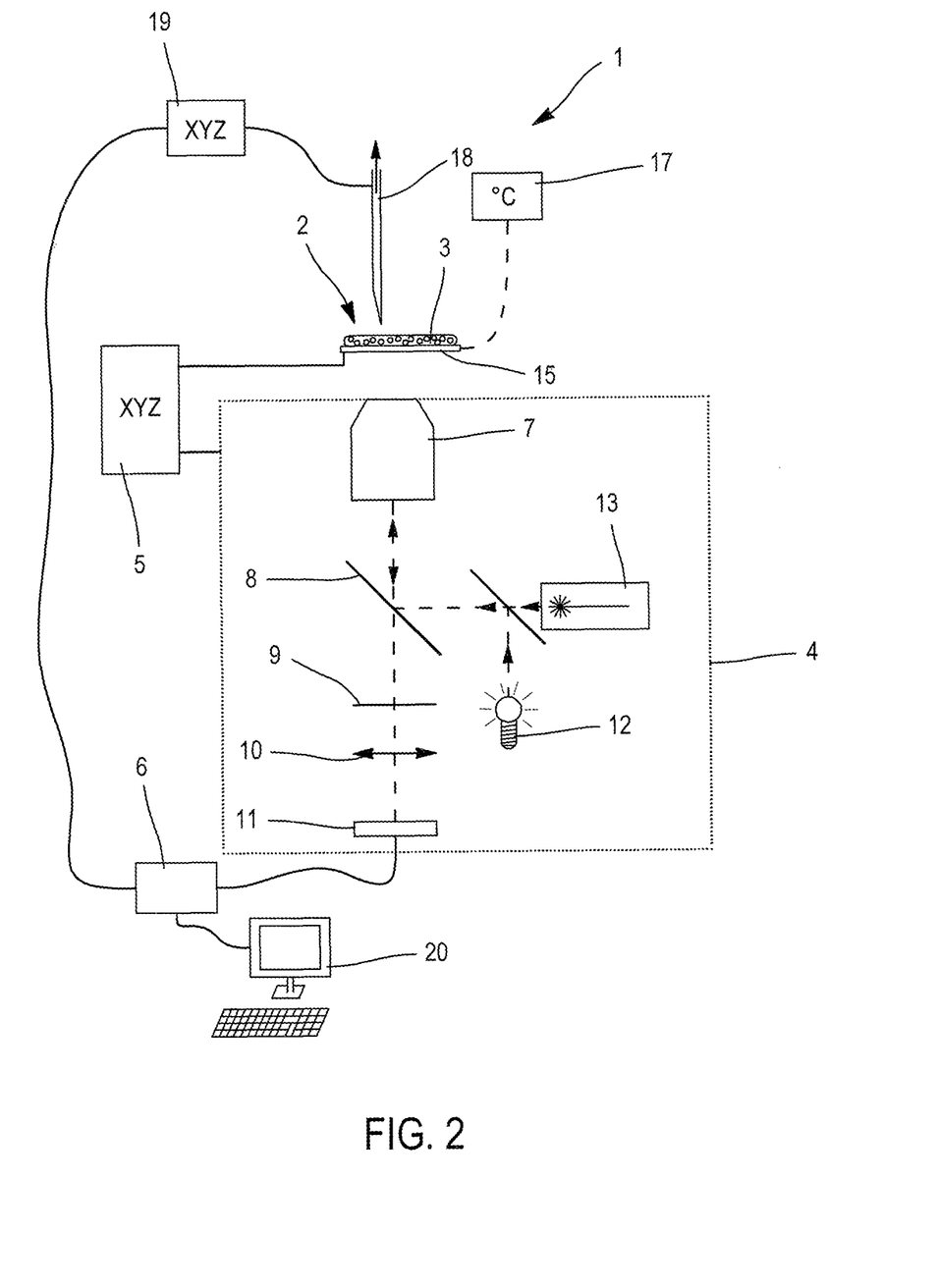

In order to allow access of micropipette 18 to the emulsion 3, plate 14 is detachable and can therefore be removed as shown in FIG. 2.

A first embodiment of the method of reading according to the invention implemented by device 1 will now be described.

This first embodiment of the method for reading the emulsion 3 according to the invention comprises:

preparing the emulsion 3 in a polydisperse coarse form, using one of the following techniques for obtaining limited shearing: electric field, ultrasounds, magnetic stirrer, or manual shearing; then placement of emulsion 3 in receptacle 2 and between the two parallel plates 14, 15; then heating the emulsion by the means 17 to a temperature above its melting point; then a shearing movement between the two plates 14, 15 until the emulsion in liquid form is monodisperse, i.e. until the standard deviation of the distribution of the diameters of the droplets 21 is less than 30% of the mean value of the diameters of the droplets 21; this shearing movement is created by the motorized means 16; then retraction of plate 14 and cooling of the emulsion by the means 17 to a temperature below its melting point, then at least one two-dimensional scanning of the emulsion by the optical system 4 by means of stage 5; during each scan, the relative position of the emulsion 3 relative to the optical system 4 changes, and for different relative positions of the emulsion 3 relative to the optical system 4, the camera 11 thus acquires different given partial images of the emulsion 3, each partial image corresponding to a given portion of the emulsion imaged by the optical system for a given relative position; for each scan, the partial images acquired during this scan are adjacent to one another and are distributed along two orthogonal scanning directions X, Y; and for each scan, construction of a two-dimensional image 24 of the emulsion from said scan, this construction comprising:

projection of the different partial images of the emulsion via the optical system 4 onto camera 11, and acquisition of these partial images by camera 11; and combining, by unit 6, the different partial images of the emulsion acquired by the camera during said scan.

Each partial image can for example correspond to a portion of the emulsion having a typical width of 100 micrometers, whereas the two-dimensional image 24 can correspond to a view of the emulsion with an area of several square centimeters. Even using an objective lens 7 with 10× magnification, an area of 3.3 mm×3.3 mm is observed per partial image, i.e. about 100 000 droplets having a diameter of 1 micrometer. It is thus possible to detect fluorescence equivalent to that of 500 molecules of fluorescein. The corresponding partial image is recorded and we move to a zone immediately adjacent before recording a new partial image. In this way it is possible to read 10 or more partial images per second for constructing a two-dimensional image, i.e. 1 million droplets 21 per second and 1 billion droplets 21 in 15 minutes.

Figure 3:
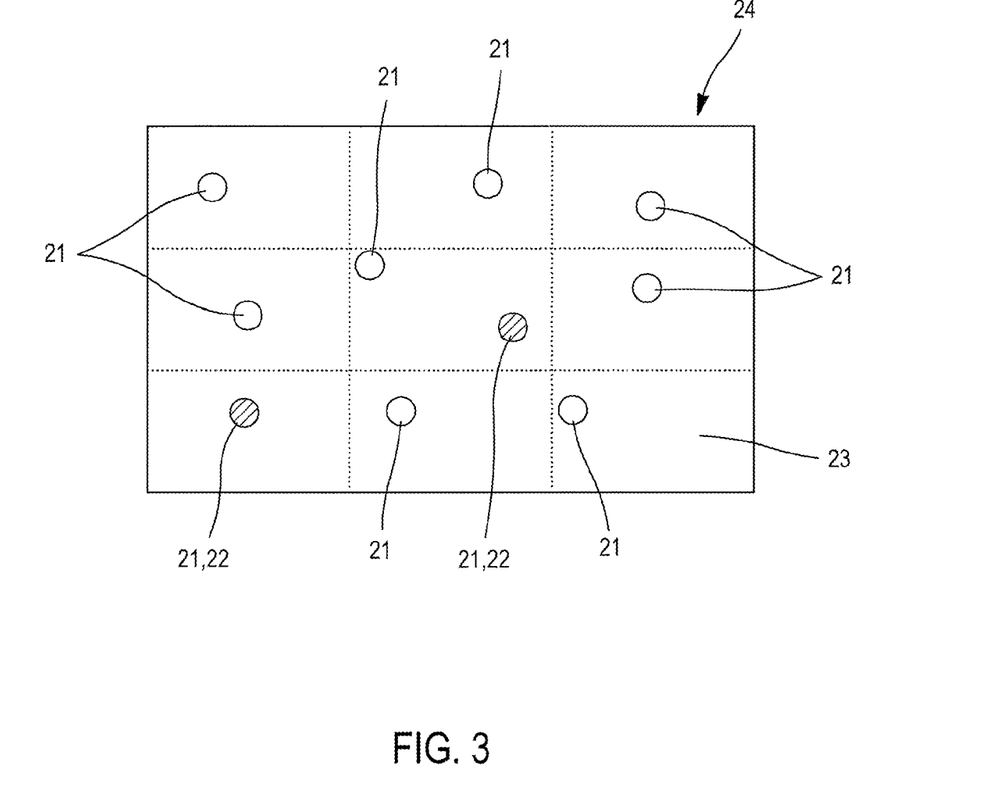
FIG. 3 illustrates a two-dimensional image of the emulsion obtained from the device of FIGS. 1 and 2 employing a first embodiment of the method according to the invention.

The two-dimensional image 24 in FIG. 3 breaks down into nine adjacent partial images delimited by dotted lines. It should be pointed out that the two-dimensional image 24 in FIG. 3 is only schematic, and that the size of the droplets 21 has been increased considerably and the number of droplets 21 has been reduced considerably for greater clarity. In fact, the two-dimensional image 24 corresponds in reality to a view of the emulsion with an area of several square centimeters, and therefore typically comprises hundreds of thousands of droplets 21 with a diameter of 1 micrometer.

In one variant, it may be sufficient to read the partial images and process them in real time, without reconstructing the large image in the form of an image file, but just so as to construct a file containing various data representative of the emulsion (such as the coordinates of specific droplets 22, the fluorescence signals, etc.).

The emulsion 3 is an inverted emulsion of water droplets 21 in an oily phase 23 called hereinafter oil 23. These droplets consist more precisely of microdroplets or microcapsules 21 having a typical diameter between 100 nanometers and 100 micrometers, preferably from 0.5 micrometer to 5 micrometers, more preferably of about 1 micrometer. For optical reasons, the optical indices of the oil 23 and of the aqueous compartments 21 are roughly equal.

Among these water droplets 21, certain specific droplets 22 contain one or more given type(s) of chemical and/or biological molecule to be located. These molecules or cells are preferably fluorescent, or are accompanied by one or more fluorescent marker(s), so as to emit a specific fluorescence signal when excited by the laser 13. These molecules or cells are preferably contained in each droplet in an amount above a certain detection threshold. Because of these molecules and/or cells, at least one chemical or biological reaction can take place in each of the specific microcapsules 22. By "biological reaction" is generally meant any reaction in molecular biology or cellular biology. Thus, each specific microcapsule 22 performs the role of an independent chemical or biochemical microreactor and makes it possible to carry out numerous reactions in parallel (up to ten billion reactions per milliliter).

A first example of reaction relates to the expression of a single gene per droplet and the field of directed evolution. Starting from a library of genes encoding for example variants of an enzyme, these genes are then expressed (by transcription/translation in vitro). The device according to the invention makes it possible to locate and sample the specific droplets 22 comprising this single gene on the basis of the activity of these enzyme variants, for example owing to a fluorescence signal emitted solely by the specific droplets 22 containing this single gene, this signal being detected by camera 11 and included in the data of the two-dimensional image 24.

A second field of application of the emulsions considered as microreactors is diagnosis and more generally the detection of molecules such as contaminants or bioterrorism agents. The droplets 21 then serve for increasing the local concentration of a product to be detected, which makes it possible to lower the detection threshold relative to bulk detection. In this case, the specific droplets 22 are droplets that contain a certain concentration of molecules or cells above their detection threshold by fluorescence. The droplets can serve as compartments for the expression in vitro of one or more reporter proteins, the expression of these proteins forming the basis of the diagnostic assay.

Compared with the methods of linear reading according to the prior art employed in a microchannel or in a "FACS", the method according to the invention therefore has the advantage of being quicker, which is particularly useful for finding rare specific droplets 22 among all of the droplets 21.

After retracting plate 14, the emulsion 3 is spread out on plate 15 so as to have a thickness less than that of 10 layers of droplets 21. A layer of droplets is a layer whose thickness is the average diameter of the droplets 21. In one variant, emulsion 3 is spread out on plate 15 in the form of a monolayer of droplets 21, i.e. the emulsion has a thickness equal to that of a single layer of droplets, as this facilitates droplet sampling by the micropipette 18. In another variant, emulsion 3 is spread out on plate 15 so as to have a thickness of several layers of droplets 21 (typically 10 layers), as this is particularly advantageous with an optical system 4 that has a depth of field roughly equal to or greater than the thickness of the spread-out emulsion: this in fact makes it possible to find specific droplets 22 in all of the layers of the emulsion 3 with a single scan, which is advantageous when the specific droplets 22 are rare.

Moreover, the emulsion comprises the continuous phase of oil 23, surrounding the droplets 21, and having a melting point (i.e. a temperature above which this oil passes from the solid state to the liquid state) above 0° C., so that generally this oil is solid at ambient temperature during scanning. More precisely, the melting point of oil 23 is above 37° C., and even above 40° C., and preferably even above 50° C.

Thus, the emulsion has a melting point (i.e. a temperature above which this emulsion passes from the solid state to the liquid state) above 0° C., so that generally the emulsion is solid at ambient temperature during scanning. By "solid" is meant a state that is non-liquid and non-gaseous. In certain particular cases, this solid state can be a gel, a glass or a crystalline state. More precisely, the melting point of the emulsion is above 37° C., and even above 40° C., or preferably even above 50° C. In this way, the emulsion can thus be heated to a temperature (typically 25° C. or 37° C.) ideal for a biological or chemical reaction while remaining solid during scanning. Thus, the method according to the invention further comprises, during each scanning of the emulsion, maintaining the emulsion at a temperature (typically 25° C. or 37° C.) below the melting point of the continuous phase 23. This maintaining is implemented by the maintaining means 17.

A formula of emulsion 3 that can be used is as follows:
the oily continuous phase 23 comprises:
   a volume fraction of Span60 in the oil of x %, with x between 0.5% and 5%, preferably roughly equal to 2.5%,
   a volume fraction of cholesterol in the oil of y %, with y between 0.5% and 5%, preferably roughly equal to 2.5%,
   a volume fraction of Dodecane in the oil of (100-x-y) %,
the droplets 21 comprise an aqueous solution comprising molecules and/or cells to be isolated in the droplets, and water.
The emulsion comprises:
   a volume fraction of water from 40% to 90%, preferably approximately 70%, which makes it possible to form droplets, and
   a volume fraction of oily phase from 10% to 60%, preferably approximately 30%.

The method according to the invention further comprises the following steps executed by the analysis unit 6 for each two-dimensional image constructed:
   locating, in the two-dimensional image 24, of the specific droplets 22 (i.e. determination of the coordinates of each specific droplet 22 in the two-dimensional image 24) by analysing the two-dimensional image 24; locating and analysis typically comprise using an algorithm for thresholding and segmentation (NIS software, from Nikon) on the two-dimensional image; typically, the specific droplets are located because they emit a specific fluorescence signal, which is detected by camera 11 and which forms part of the data of the two-dimensional image: the laser 13 emits radiation that excites molecules, cells and/or fluorescent markers contained in the specific droplets 22, the filter 9 allows the fluorescence signal emitted by each specific droplet 22 to pass but blocks the wavelengths emitted by laser 13, so that the camera detects each specific fluorescence signal, then unit 6 records the spatial coordinates and the values of each specific fluorescence signal as forming part of the data of the two-dimensional image;

counting, in the two-dimensional image 24, of the specific droplets 22 (i.e. calculation of the number of specific droplets 22 in the two-dimensional image 24) by analysing the two-dimensional image of the emulsion; counting and analysis typically comprise using an algorithm for thresholding and segmentation (NIS software, from Nikon) on the two-dimensional image.

In a first variant, the method according to the invention then comprises sampling of one or more of the specific droplets 22, the sampling of each droplet 22 comprising:

movement of the end of micropipette 18 to coordinates where a specific droplet 22 has been located; the micropipette is moved by the stage 19, and this movement is automated because after locating a specific droplet 22, the analysis unit 6 communicates the coordinates of this droplet 22 directly to the stage 19; and aspiration of this specific droplet 22 along the micropipette 18.

Thus, a small number of droplets 22, relative to the total number of droplets 21 read, are taken one by one, by the suction means. Typically, fewer than 10,000, preferably fewer than 1,000 or fewer than 100 droplets 22 are taken. When these droplets 22 that are taken each contain a gene, these genes can then be amplified (after removing the oil phase) by one of the techniques of gene amplification of the single molecule type (for example: "single molecule PCR", "single molecule emulsion PCR").

In a second variant, which can be combined with the first variant, the method according to the invention further comprises time-based monitoring of a chemical or biological reaction taking place in at least one of the specific droplets 22, said monitoring comprising repetition of the steps of scanning and construction, and optionally of locating and/or of counting. To perform this monitoring, unit 7 stores and compares successive different two-dimensional images constructed by this unit 6.

As the emulsion 3 is solid during and between all the scans performed for monitoring the reaction, the droplets 21 do not move and therefore each droplet 21 can be identified unequivocally, permitting kinetic monitoring (not possible using FACS). Use of a solid emulsion also makes it possible to prevent any exchange of solutes between the droplets. As the droplets 21 do not move, the variation in fluorescence of each of these thousands of droplets 21 over time can be detected immediately.

A second embodiment of the method of reading according to the invention implemented by means of device 1 will now be described, referring to FIGS. 4 to 8. This second embodiment will only be described with respect to its differences relative to the first embodiment described above.

In the first embodiment of the method according to the invention, the continuous phase 23 was solidified, in order to "freeze" the droplets 21. The droplets are frozen by the means 17.

In the second embodiment of the method according to the invention, the droplets are frozen using a semi-compact or compact network of droplets, so that the droplets are blocked by one another. The droplets are frozen by the compact or semi-compact network of droplets, and by the means 17, 14, and 15 as described hereunder.

Figure 4:
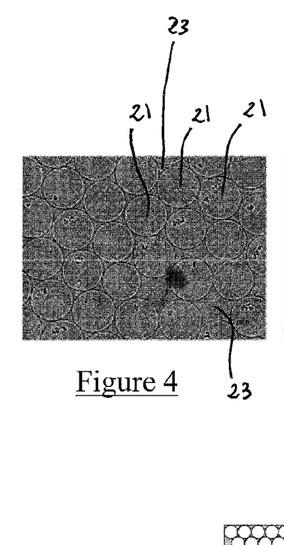
FIG. 4 illustrates a network of droplets of an emulsion.
Figure 5:
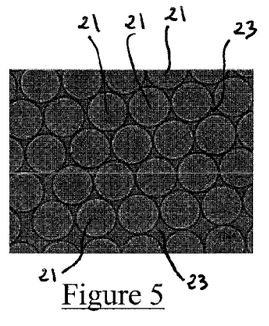
FIGS. 5 and 6 illustrate different variants of networks of droplets of an emulsion placed in the device of FIGS. 1 and 2 for implementing a second embodiment of the method according to the invention.
Figure 6:
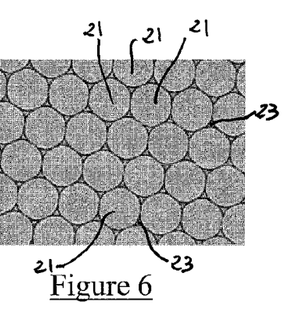

FIGS. 4 to 6 illustrate different variants of the emulsion 3 that can be placed in receptacle 2 of device 1 and the droplets of which form a two-dimensional network of droplets. Droplets are said to form a two-dimensional network if for any one of these droplets, this droplet is tangential to at least two other droplets, these three tangential droplets not being aligned. In these diagrams, the average diameter of the droplets 21 in the continuous phase 23 is about 60 micrometers.

The volume fraction $\Phi$ of the droplets in the emulsion is, for a given volume of emulsion, the ratio of:

on the one hand, the sum of the volume of droplets contained in this volume of emulsion, to on the other hand, this volume of emulsion.

FIG. 4 illustrates the case when the volume fraction of the droplets 21 is less than 40%.

In implementing the second embodiment of the method according to the invention, the volume fraction of the droplets 21 is greater than or equal to 40%, and is preferably greater than or equal to 60%.

For a volume fraction of droplets between 40% and 60%, as illustrated in FIG. 5, the droplets are said to form a semi-compact two-dimensional network of droplets.

For a volume fraction of droplets greater than or equal to 60%, as illustrated in FIG. 6, the droplets are said to form a compact two-dimensional network of droplets.

For a volume fraction of droplets greater than or equal to 60%, as illustrated in FIG. 6, the droplets 21 of the emulsion form a colloidal solid, i.e. they are suspended in the continuous phase 23 but at such a density that they can no longer undergo rearrangement in the network of droplets: they are blocked by one another and are "frozen" like the molecules in a solid.

For implementing the second embodiment of the method according to the invention, the continuous phase 23 comprises a surfactant in order to stabilize the droplets 21 and prevent them coalescing, which would lead to collapse of the network of droplets by phase separation (i.e. creation of an oil continuous phase and of a separate, aqueous continuous phase). By "surfactant" is meant a surface-active compound that alters the surface tension that is exerted between each droplet and the continuous phase 23, so as to stabilize the emulsion and avoid coalescence of the droplets, for example a surfactant belonging to the SPAN series (for example SPAN 60, SPAN 80, etc.).

A formula of the emulsion 3 that can be used for the second embodiment of the method according to the invention is as follows:

the fluorocarbon oily continuous phase 23 comprises:
  a fluorinated oil (for example Fluoroinert FC-3283, from 3M)
  a fluorinated surfactant made from the ammonium salt of a perfluorinated polyether (for example Krytox FSL from Dupont), the mass fraction of surfactant in the oil being x %, with x between 0.5% and 5%, preferably roughly equal to 2%, the droplets 21 comprise an aqueous solution comprising molecules and/or cells to be isolated in the droplets, and water.

The emulsion comprises:
  a volume fraction of water from 40% to 90%, preferably approximately 70%, which makes it possible to form droplets, and
  a volume fraction of oily phase from 10% to 60%, preferably approximately 30%.

Figure 7:
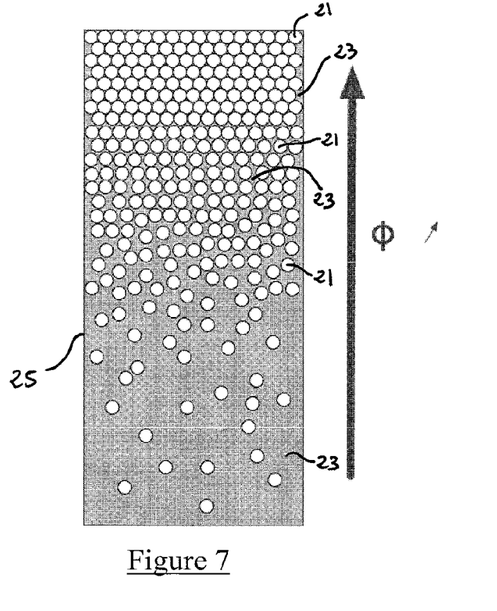
FIG. 7 illustrates a creaming chamber or a sedimentation chamber for implementing the second embodiment of the method according to the invention.

The second embodiment of the method for reading the emulsion 3 according to the invention comprises:

preparation of the emulsion 3 in a coarse polydisperse form, using for example one of the following techniques for obtaining limited shearing: electric field, ultrasounds, magnetic stirrer, or manual shearing; it is preferable to use shearing of an aqueous disperse phase in an oil continuous phase, and a "hydrodynamic focusing" technique, for example as described in the article of Shelley L. Anna et al. with the title "Formation of dispersions using flow focusing in microchannels" published in APPLIED PHYSICS LETTERS, 2003, 82, 364-366; then the emulsion prepared is placed in a creaming or sedimentation chamber depending on the density difference between the continuous phase 23 and the disperse phase i.e. the droplets 21. The droplets 21 are subject to the force of gravity and the Archimedes force. The direction of movement of the droplets simply depends on the density difference between the two phases. In the case when the droplets 21 have a lower density than the continuous phase 23, the droplets move oppositely to gravity, they cream, and a creaming chamber is used. In the opposite case, when the droplets 21 have a higher density than the continuous phase 23, the droplets move in the direction of gravity, they settle, and a sedimentation chamber is used. Competition between the Archimedes force and the viscous forces due to drainage of the oil film and interactions between the droplets 21 results in the creation of a droplet concentration gradient and thus stratification. FIG. 7 illustrates a creaming chamber 25 in which the volume fraction of droplets Φ increases in a direction opposite to gravity. In order to obtain a network of droplets 21 with a desired degree of compaction, a pipette 18 is used for collecting droplets 21 from chamber 25 at the level of a layer which has, locally, a desired volume fraction of droplets Φ (i.e. a concentration of droplets) greater than or equal to 40%, preferably greater than or equal to 60%, and the droplets taken are injected into receptacle 2.

then, while the emulsion is stored in the receptacle, at least one two-dimensional scanning of the emulsion is carried out, and for each scan, a two-dimensional image 24 of the emulsion is constructed from said scan, as described for the first embodiment of the method according to the invention.

During each scan, the forces that can move the droplets 21 in the emulsion are reduced. These forces are in particular generated by gravity and by compression/expansion of receptacle 2 due to thermal fluctuations. Thus, to reduce these forces and to freeze the droplets:

during scanning of the emulsion, receptacle 2 is maintained at a roughly constant temperature by the means 17, preferably to an accuracy of plus or minus 0.1° C.;

plate 15 comprises a flat wall, which is in contact with the emulsion during scanning of the emulsion and is arranged horizontally with a vertical difference in level of less than 5 micrometers over a horizontal distance of 2 centimeters; and plates 14 and 15 are parallel and, during scanning of the emulsion, hold each of the droplets 21; in other words, receptacle 2 has a vertical thickness separating the plates 14, 15 less than the average diameter of the unstressed droplets 21, so that emulsion 3 is spread out on plate 15 in the form of a monolayer of droplets 21 and so that the droplets 21 are subject to a vertical stress, so that the droplets 21 are confined vertically and are no longer spherical but are like "pancakes".

Moreover, the second embodiment can comprise other steps, for example:

analysis of the two-dimensional image (locating, counting, etc.) as described previously for the first embodiment of the method according to the invention; and/or time-based monitoring of a chemical or biological reaction as described previously for the first embodiment of the method according to the invention: in the second embodiment of the method according to the invention, the droplets form a compact or semi-compact network; during and between all the scans performed for monitoring a reaction, the droplets 21 do not move and therefore each droplet 21 can be identified unequivocally by associating each droplet with a position in the two-dimensional network of droplets, providing spatial and temporal detection of each droplet, and which therefore permits kinetic monitoring (not possible with FACS); as the droplets 21 do not move, the variation in fluorescence of each of these thousands of droplets 21 over time can be detected immediately; and/or sampling of droplets as described previously for the first embodiment of the method according to the invention.

Figure 8:
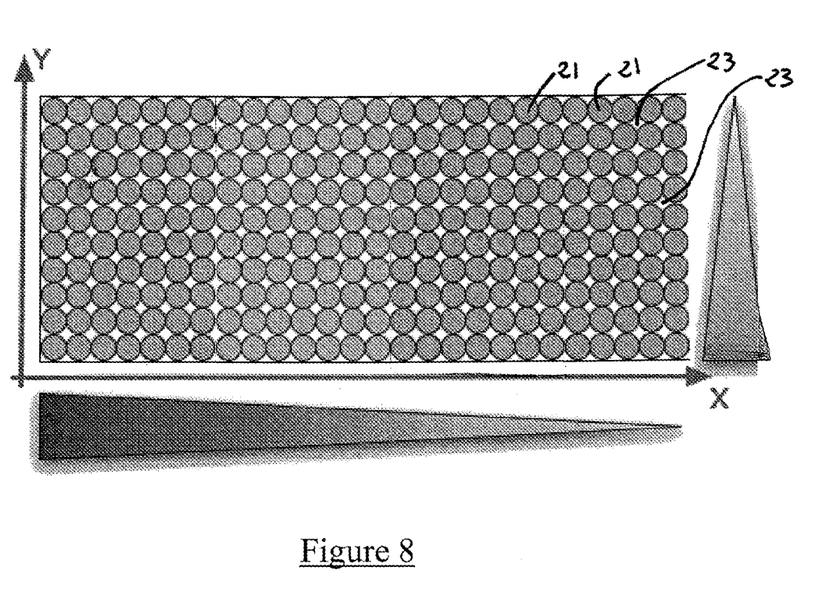
FIG. 8 illustrates a network of droplets placed in the device of FIGS. 1 and 2.

Advantageously, referring to FIG. 8:

each of the droplets comprises a certain amount of a first compound A and a certain amount of a second compound B, and the two-dimensional network of droplets 21 contained in a plane defined by the different axes X and Y is such that, from one droplet to another, there is a gradient of compound A along axis X and a gradient of compound B along axis Y;

thus, a different composition of compounds A and B is obtained for each position in the two-dimensional network of droplets, and a phase diagram of compounds A and B is constructed by scanning the network of droplets. The content of droplets is inhomogeneous from one droplet to another. Inhomogeneity of the content of droplets is a property that is utilized for making phase diagrams in two dimensions. One droplet is associated with one composition (chemical or biological for example), making it possible to investigate and screen a large number of combinations of compounds.

An example of application of the first and/or second embodiment of the method according to the invention will now be described, with reference to FIGS. 9 to 11:

comprising time-based monitoring of kinetics such as cell growth of a yeast, and in which the droplets do not move during a scan and between the successive scans of time-based monitoring, and therefore in which a droplet corresponds to a given position.

In this example, each droplet contains initially (at t=0) 0 or 1 fluorescent yeast.

Figure 9:
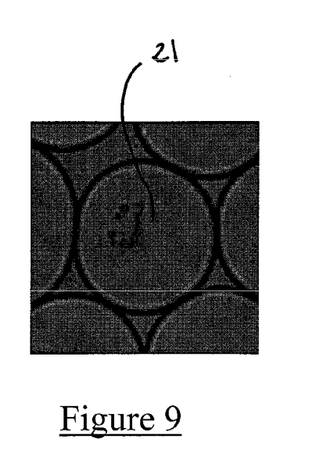
FIG. 9 shows an enlargement of a droplet comprising fluorescent yeast.
Figure 10:
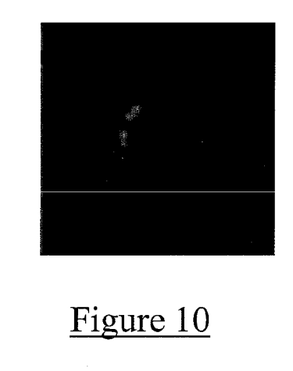
FIG. 10 is an image of the fluorescence emitted by the droplet of FIG. 9.

FIG. 9 is a view in white light of a droplet 21 containing 4 yeasts at a given instant t>0, said droplet containing initially at t=0 a single fluorescent yeast.

FIG. 9 is an image of the fluorescence emitted by this droplet 21.

Figure 11:
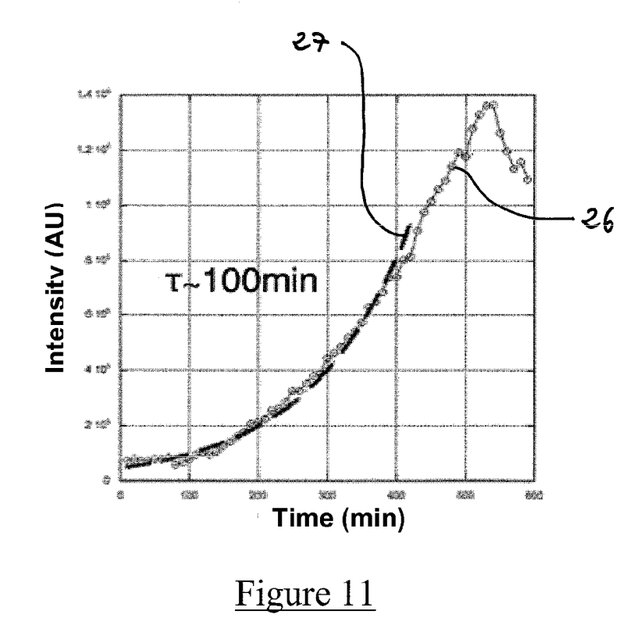
FIG. 11 illustrates the luminous fluorescence intensity emitted from the droplet of FIG. 9 as a function of time.

FIG. 11 shows a curve 26 of cumulative fluorescence intensity for all the yeasts of this droplet 21 in an arbitrary unit as a function of time in minutes, and is representative of the growth of the yeasts in this droplet 21 over time. This curve is extracted from an analysis of the two-dimensional images of the emulsion as a function of time. FIG. 11 further comprises an exponential interpolation 27 of this curve, which gives access to an average division time of 100 minutes.

By accumulating such data 26, 27 for each of the droplets of the emulsion, the method according to the invention does of course make it possible to calculate an average division time of the yeasts, but also a statistical distribution of these times. The invention therefore provides parallel monitoring in time of a very large number of well-controlled events occurring in droplets "frozen" at well-defined positions.

Of course, the invention is not limited to the examples that have just been described, and numerous adjustments can be made to these examples without exceeding the scope of the invention.

In particular, the micropipette 18 of device 1 can be replaced by any other device for micromanipulation known to a person skilled in the art.

Moreover, in one variant, the micropipette 18 or any other device for micromanipulation replacing it is stationary, and the stage 19 moves the plate 15 relative to the device for micromanipulation 18.

Finally, the first and second embodiments of the method according to the invention described above are compatible: it is in fact possible to "freeze" droplets 21 of an emulsion forming a compact or semi-compact two-dimensional network of droplets by solidifying a continuous phase 23 that surrounds said droplets 21.

The invention claimed is:

1. A method for reading an emulsion comprising droplets and a continuous phase which surrounds the droplets, said method comprising:
    two-dimensional scanning the emulsion with an optical system, the emulsion being maintained during the scanning at a temperature below the melting point of the continuous phase; and
    constructing a two-dimensional image of the emulsion based on said scanning.

2. The method according to claim 1, wherein the droplets do not move during scanning.

3. The method according to claim 1, wherein the continuous phase is solid during scanning.

4. The method according to claim 1, wherein the continuous phase has a melting point above 37° C.

5. The method according to claim 1, wherein the continuous phase has a melting point above 40° C.

6. The method according to claim 1, wherein the continuous phase has a melting point above 50° C.

7. The method according to claim 1, wherein the droplets of the emulsion form a two-dimensional network of droplets.

8. The method according to claim 7, wherein the volume fraction of droplets in the emulsion is greater than or equal to 40%.

9. The method according to claim 7, wherein the volume fraction of droplets in the emulsion is greater than or equal to 60%.

10. The method according to claim 1, wherein the droplets of the emulsion form a colloidal solid.

11. The method according to claim 1, wherein the continuous phase comprises a surfactant.

12. The method according to claim 1, wherein during scanning of the emulsion, the emulsion is stored in a receptacle.

13. The method according to claim 12, wherein during scanning of the emulsion, the receptacle is maintained at a roughly constant temperature, to an accuracy of plus or minus 0.1° C.

14. The method according to claim 12, wherein the receptacle comprises a flat wall, which during scanning of the emulsion is in contact with the emulsion and is arranged horizontally with a vertical difference in level of less than 5 micrometers over a horizontal distance of 2 centimeters.

15. The method according to claim 12, wherein the receptacle comprises two approximately parallel surfaces which during scanning of the emulsion hold each of the droplets in place.

16. The method according to claim 1, further comprising time-based monitoring of a chemical or biological reaction taking place in at least one of the droplets, said monitoring comprising repeating the two-dimensional scanning and the constructing a two-dimensional image steps.

17. The method according to claim 1, further comprising locating droplets comprising a given type of molecule or cell by analysing the two-dimensional image of the emulsion.

18. The method according to claim 17, wherein said locating the droplets utilizes an algorithm for thresholding and segmentation of the two-dimensional image.

19. The method according to claim 1, further comprising sampling the droplets comprising a given type of molecule or cell.

20. The method according to claim 19, wherein said sampling the droplets comprises:
    moving one end of a micropipette to coordinates where a droplet comprising the given type of molecule or cell has been located, and
    aspirating said droplet with the micropipette.

21. The method according to claim 1, further comprising counting the droplets comprising a given type of molecule or cell by analysing the two-dimensional image of the emulsion.

22. The method according to claim 21, wherein said counting the droplets utilizes an algorithm for thresholding and segmentation of the two-dimensional image.

23. The method according to claim 1, wherein constructing the two-dimensional image comprises, during scanning:
    projecting different partial images of the emulsion via the optical system onto a detector, and
    combining the different partial images of the emulsion acquired by the detector.

24. The method according to claim 23, wherein the partial images are images of fluorescence signals emitted by the emulsion.

25. The method according to claim 1, wherein the emulsion is an inverted emulsion of water droplets in oil.

26. The method according to claim 1, wherein the emulsion is spread out so as to have a thickness between 1 and 100 layers of droplets.

27. The method according to claim 26, wherein the optical system has a depth of field roughly equal to or greater than the thickness of the spread-out emulsion.

28. The method according to claim 1, further comprising:
    placing the emulsion between two parallel plates, at least one of said plates being transparent,
    applying a shearing movement between the two plates until the emulsion is monodisperse.

29. A device for reading an emulsion comprising droplets and a continuous phase which surrounds the droplets, said device comprising:
    a receptacle configured to receive the emulsion;
    an optical system;
    means for carrying out two-dimensional scanning of the emulsion by the optical system;
    means for maintaining the emulsion at a temperature below the melting point of the continuous phase during the scanning of the emulsion; and
    means for constructing a two-dimensional image of the emulsion based on the two-dimensional scan of the emulsion.

30. The device according to claim 29, further comprising means for "freezing" the droplets during scanning.

31. The device according to claim 29, further comprising means for preparing the emulsion, said means for preparing the emulsion being arranged so that the droplets of the emulsion form a two-dimensional network of droplets.

32. The device according to claim 31, wherein the means for preparing the emulsion comprise a chamber for creaming or sedimentation of the droplets and means for sampling, from said chamber, droplets diluted in the continuous phase according to a given volume fraction of droplets.

33. The device according to claim 29, further comprising means for maintaining the receptacle at a roughly constant temperature during scanning of the emulsion, at an accuracy of plus or minus 0.1° C.

34. The device according to claim 29, wherein the receptacle comprises a flat wall arranged to be in contact with the emulsion during scanning of the emulsion and is arranged horizontally with a vertical difference in level of less than 5 micrometers over a horizontal distance of 2 centimeters.

35. The device according to claim 29, wherein the receptacle comprises two approximately parallel surfaces arranged to hold each of the droplets in place during scanning of the emulsion.

36. The device according to claim 29, further comprising means for time-based monitoring of a chemical or biological reaction taking place in at least one of the droplets.

37. The device according to claim 29, further comprising means for locating droplets comprising a given type of molecule or cell, the locating means comprising means for analysing the two-dimensional image of the emulsion.

38. The device according to claim 29, further comprising means for sampling droplets comprising the given type of molecule or cell.

39. The device according to claim 38, wherein the means for sampling droplets comprise:
a micropipette,
means for moving an end of the micropipette to coordinates of the droplet comprising the given type of molecule or cell and that has been located by locating means, and
means for aspirating said droplet with the micropipette.

40. The device according to claim 29, further comprising means for counting droplets comprising a given type of molecule or cell, said means for counting droplets comprising means for analysing the two-dimensional image of the emulsion.

41. The device according to claim 29, wherein the means for constructing the two-dimensional image comprise:
a detector on which the optical system is set up for projecting different partial images of the emulsion during a scan, and
means for combining the different partial images of the emulsion acquired by the detector during scanning.

42. The device according to claim 29, wherein the receptacle is arranged so that the emulsion is spread out so as to have a thickness between 1 and 100 layers of droplets.

43. The device according to claim 42, wherein the optical system has a depth of field roughly equal to or greater than the thickness of the spread-out emulsion.

44. The device according to claim 29, wherein the receptacle comprises two parallel plates, at least one of said plates being transparent, and means for applying a shearing movement between the two plates until the emulsion is monodisperse.

45. A method for reading an emulsion comprising droplets and a continuous phase which surrounds the droplets, said method comprising:

two-dimensional scanning the emulsion with an optical system, the droplets of the emulsion forming a two-dimensional network of droplets; and
constructing a two-dimensional image of the emulsion based on said scanning.

46. The method according to claim 45, wherein the droplets do not move during scanning.

47. The method according to claim 45, wherein the continuous phase is solid during scanning.

48. The method according to claim 45, wherein the continuous phase has a melting point above 37° C.

49. The method according to claim 45, wherein the continuous phase has a melting point above 40° C.

50. The method according to claim 45, wherein the continuous phase has a melting point above 50° C.

51. The method according to claim 45, wherein the emulsion is maintained at a temperature below the melting point of the continuous phase.

52. The method according to claim 51, wherein the volume fraction of droplets in the emulsion is greater than or equal to 40%.

53. The method according to claim 51, wherein the volume fraction of droplets in the emulsion is greater than or equal to 60%.

54. The method according to claim 45, wherein the droplets of the emulsion form a colloidal solid.

55. The method according to claim 45, wherein the continuous phase comprises a surfactant.

56. The method according to claim 45, wherein during scanning of the emulsion, the emulsion is stored in a receptacle.

57. The method according to claim 56, wherein during scanning of the emulsion, the receptacle is maintained at a roughly constant temperature, to an accuracy of plus or minus 0.1° C.

58. The method according to claim 56, wherein the receptacle comprises a flat wall, which during scanning of the emulsion is in contact with the emulsion and is arranged horizontally with a vertical difference in level of less than 5 micrometers over a horizontal distance of 2 centimeters.

59. The method according to claim 56, wherein the receptacle comprises two approximately parallel surfaces which during scanning of the emulsion hold each of the droplets in place.

60. The method according to claim 45, further comprising time-based monitoring of a chemical or biological reaction taking place in at least one of the droplets, said monitoring comprising repeating the two-dimensional scanning and the constructing a two-dimensional image steps.

61. The method according to claim 45, further comprising locating droplets comprising a given type of molecule or cell by analysing the two-dimensional image of the emulsion.

62. The method according to claim 61, wherein said locating the droplets utilizes an algorithm for thresholding and segmentation of the two-dimensional image.

63. The method according to claim 45, further comprising sampling the droplets comprising a given type of molecule or cell.

64. The method according to claim 63, wherein said sampling the droplets comprises:
moving one end of a micropipette to coordinates where the droplet comprising the given type of molecule or cell has been located, and
aspirating said droplet with the micropipette.

65. The method according to claim 45, further comprising counting the droplets comprising a given type of molecule or cell by analysing the two-dimensional image of the emulsion.

66. The method according to claim 65, wherein said counting the droplets utilizes an algorithm for thresholding and segmentation of the two-dimensional image.

67. The method according to claim 45, wherein constructing the two-dimensional image comprises, during scanning:
   projecting different partial images of the emulsion via the optical system onto a detector, and
   combining the different partial images of the emulsion acquired by the detector.

68. The method according to claim 67, wherein the partial images are images of fluorescence signals emitted by the emulsion.

69. The method according to claim 45, wherein the emulsion is an inverted emulsion of water droplets in oil.

70. The method according to claim 47, wherein the emulsion is spread out so as to have a thickness between 1 and 100 layers of droplets.

71. The method according to claim 70, wherein the optical system has a depth of field roughly equal to or greater than the thickness of the spread-out emulsion.

72. The method according to claim 47, further comprising:
   placing the emulsion between two parallel plates, at least one of said plates being transparent,
   applying a shearing movement between the two plates until the emulsion is monodisperse.

* * * * *